United States Patent [19]

Seppi

[11] 4,452,081

[45] Jun. 5, 1984

[54] MEASUREMENT OF VELOCITY AND TISSUE TEMPERATURE BY ULTRASOUND

[75] Inventor: Edward J. Seppi, Menlo Park, Calif.

[73] Assignee: Varian Associates, Inc., Palo Alto, Calif.

[21] Appl. No.: 429,579

[22] Filed: Sep. 30, 1982

[51] Int. Cl.³ .................. G01N 29/00; G01K 11/22
[52] U.S. Cl. .................................. 73/597; 128/660; 128/736; 374/119
[58] Field of Search ............. 374/117, 119; 73/597; 128/660, 736; 367/27

[56] References Cited

U.S. PATENT DOCUMENTS

| | | | |
|---|---|---|---|
| 2,934,756 | 4/1960 | Kalmus | 374/119 |
| 3,257,639 | 6/1966 | Kokesh | 367/27 |
| 3,302,166 | 1/1967 | Zemanek, Jr. | 367/27 |
| 4,215,575 | 8/1980 | Akita et al. | 374/119 |

OTHER PUBLICATIONS

"New Sensors for Ultrasound: Measuring Temperature Profiles", Lynnworth et al., *Materials Evaluation and Standards*, Aug. 1970, vol. 10, No. 8, pp. 6–11.

*Primary Examiner*—Howard A. Birmiel
*Attorney, Agent, or Firm*—Stanley Z. Cole; Keiichi Nishimura

[57] ABSTRACT

Temperature inside a tissue volume is noninvasively determined on the basis of its known relationship with the velocity of ultrasound inside the volume. The velocity of ultrasound between two field points inside the volume of interest is calculated from measurements of differences in transit times of sound beams scattered in substantially opposite directions at these field points.

11 Claims, 3 Drawing Figures

SPEED OF SOUND VS. TEMPERATURE IN VIVO RUNS

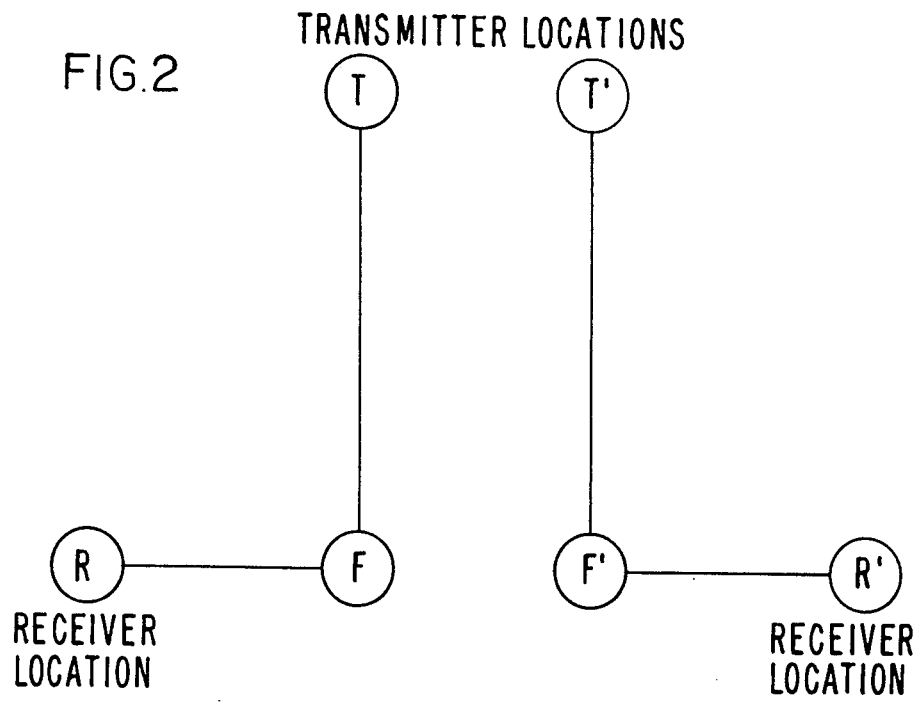
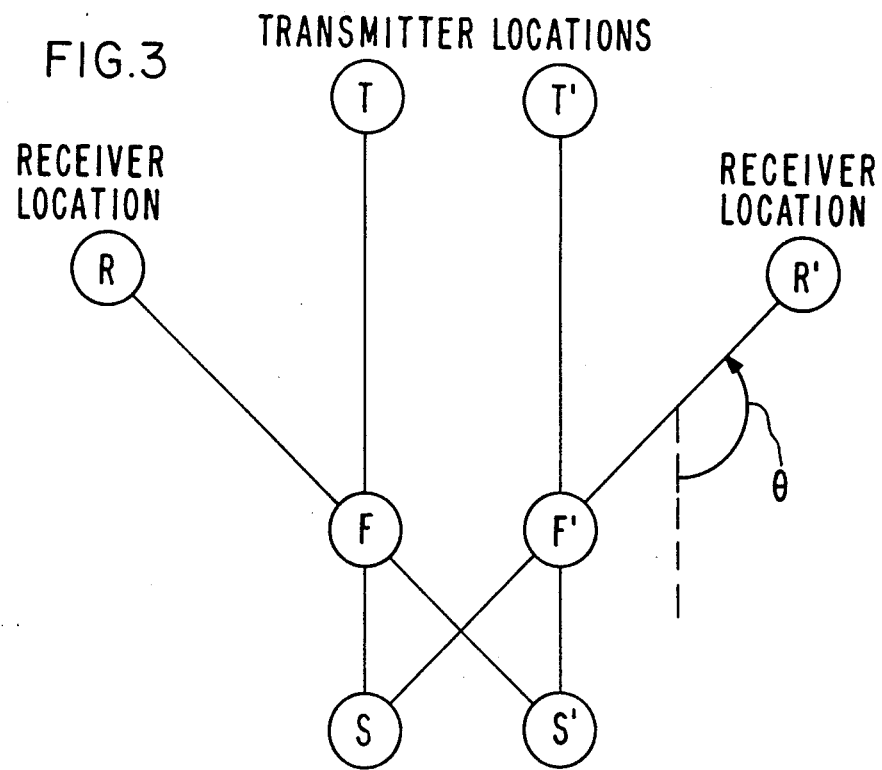

MEASUREMENT OF VELOCITY AND TISSUE TEMPERATURE BY ULTRASOUND

BACKGROUND OF THE INVENTION

This invention relates to a noninvasive method of measuring temperature by using ultrasound and more particularly to a method of determining local tissue temperature in the application of hyperthermia techniques by measuring the velocity of ultrasound in the region of interest.

It is important in the application of hyperthermia techniques using ultrasonic or microwave applicators to monitor the temperature of internal tissue structures as they are being treated. Although interactions of ultrasound with tissue are mostly insensitive to temperature, it has been found that the velocity of sound in various tissue structures is dependent upon temperature and attempts have been made to develop techniques for measuring the average local velocity of sound in a defined spatial volume of tissue in order to determine the temperature and/or other physical characteristics of the tissue from the results of such measurement.

Such techniques have typically involved the use of computed tomography principles for the measurement of the local velocity within small elements throughout the entire cross sectional region of the anatomy of interest. By such techniques, the transit time required to traverse the plane region of interest is measured in all directions. This may be done, for example, in a parallel or fan beam geometry as in the case of standard X-ray CT systems. These resulting transit times correspond to the line integrals for X-ray attenuation and in principle can be substituted into a reconstruction algorithm for yielding results corresponding to the local ultrasound velocity within small elements throughout the plane region which has been measured. An important problem with this technique is the effects of refractions which cause the rays to travel along a curved path, thereby making image reconstruction difficult, if not impossible.

SUMMARY OF THE INVENTION

It is an object of the present invention to provide a noninvasive method of determining the temperature of an internal tissue structure by measuring the local propagation velocity of sound through an elemental volume of such tissue structure.

It is another object of the present invention to provide beam geometries according to which the velocity of sound propagation through a tissue structure can be measured accurately and easily without the complication of the computerized tomography system.

BRIEF DESCRIPTION OF THE DRAWINGS

FIG. 2 shows an experimental arrangement of transmitter and receiver transducers embodying the present invention.

FIG. 3 shows another experimental arrangement of transmitter and receiver transducers embodying the present invention.

DETAILED DESCRIPTION OF THE INVENTION

Figure 1:
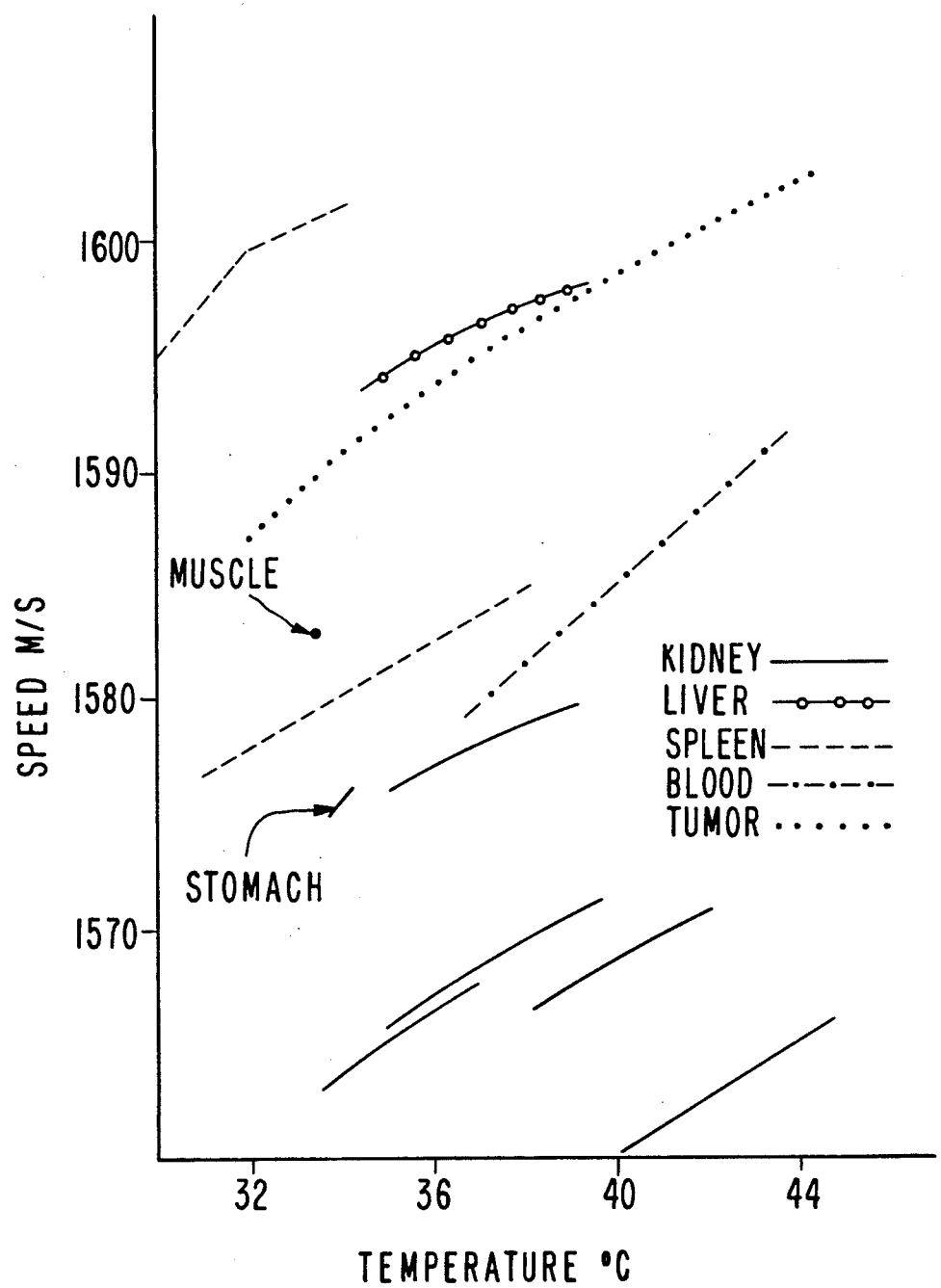
FIG. 1 shows some typical relationships between the velocity of sound and temperature in various tissues.

According to the present invention, local temperature of a medium such as a tissue structure is determined on the basis of a known relationship between the velocity of ultrasound and temperature in that medium. FIG. 1 shows some typical examples of such relationships and the problem of determining temperature is thereby reduced to that of measuring the velocity of ultrasound inside the medium. This is accomplished as shown below by indirectly measuring the transit time of ultrasound between two points separated by a predetermined distance inside the medium and by taking the ratio of this distance to the measured transit time.

Referring now to FIG. 2 which illustrates the principle embodying the present invention, field positions F and F' are two points within the medium the temperature of which is being sought. An ultrasound transmitter such as a transmitter transducer is first positioned at point T, line segment TF being preferably perpendicular to line segment FF', and directed towards F, i.e. the transducer is adapted to transmit a sharply focused beam along line TF. Two receiver transducers are used, one located at position R and directed toward F, i.e. adapted to receive ultrasound energy traveling along line FR, and the other located at position R' and directed also towards F. Points R, F, F' and R' lie in this order on a single straight line which is perpendicular to line TF. Transit times $t_{TR}$ and $t_{TR'}$ of ultrasound energy from T to R and R', respectively, are measured with this arrangement by any known method. Since the transmitter transducer at T transmits a sharply defined beam and each receiver transducer is adapted to detect only ultrasound energy traveling (oppositely) along the direction of its orientation, $t_{TR}$ is the sum of the transit time between T and F and that between F and R while $t_{TR'}$ is similarly the sum of the transit time between T and F and that between F and R'.

Next, the transmitter transducer is moved from T to T' and directed towards F', lines TF and T'F' being preferably parallel to each other. Transit times $t_{T'R}$ and $t_{T'R'}$ of ultrasound energy from T' to R and R', respectively, are measured similarly as above. The transit time $t_{FF'}$ of ultrasound energy between F and F' is now obtained by the following equation:

$$t_{FF'} = [(t_{T'R} - t_{TR}) + (t_{TR'} - t_{T'R'})]/2. \qquad (1)$$

Inside each pair of parentheses is an indirectly measured value of transit time between F and F' so that Equation (1) is essentially in the form of an average of two indirectly measured transit times between F and F'.

The advantage of using the method described above is that the desired transit time is not measured directly but is given as a difference between measured quantities. It thus becomes possible to use interference or phase shift measurement techniques instead of directly measuring two transit times and numerically subtracting one from the other. The use of difference measurement techniques can also eliminate certain systematic errors. In fact, line segments TF and T'F' do not have to be parallel to each other or of same length because the transit time between T and F is cancelled out in the above equation. Similarly, line segments FR and F'R' clearly need not be of same length.

In a typical application, the separation between field points F and F' may be about 1.5 centimeters. Since the velocity of sound is about 1.5 millimeters/microsecond, transit time $t_{FF'}$ is about 10 microseconds. The relative change in velocity per degree in a typical tissue is about 0.001 degree $^{-1}$. This means that the transit time through the volume of interest changes by ten nanoseconds per degree celsius change in local temperature. At $2.5 \times 10^6$ cycles/sec, this corresponds to about 9° in phase per degree celsius. Since the wavelength is about 0.6 millimeters at this frequency, dimensions must be kept constant to approximately $0.6 \times (9/360) = 0.015$ millimeters for measurements with accuracies of the order of 1 degree celsius.

FIG. 3 shows an alternative experimental arrangement in which the scattering angle is not 90°. Symbols T, T', F and F' have the same meanings as in FIG. 2. R and R' are new receiver positions where receiver transducers are located to receive ultrasound energy traveling along lines FR and F'R', respectively. Points R and R' lie on the plane defined by T, T', F and F'. Directions TF and FR make angle theta, and so do directions T'F' and F'R'. Position S is where extended lines TF and F'R' cross each other and position S' is similarly defined as the intersection of extended lines T'F' and FR. If S and S' may be considered to lie inside the same region as F and F' that has constant ultrasonic velocity, $$t_{FF}[(1+|\cos\theta|)/\sin\theta)] = (t_{TR} + t_{TR'} - t_{TR} - t_{TR'})/2. \quad (2)$$

The value of the expression inside the brackets gives an indication of the sensitivity of the experiment to the scattering angle theta. For scattering angles approximately in the range between 60° and 120°, the value of the expression is less than 2 and is relatively slow-varying. Thus, the scattering angle should preferably be chosen in this range in order not to have the accuracy of measurements significantly impaired.

As commented above in connection with Equation (1), the right hand side of Equation (2) is in the form of an average of two differences in transit times so that the same types of systematic errors of measurement can be eliminated. For example, line segments TF and T'F' and line segments FR and F'R' need not be of same lengths.

The present invention has been described above in terms of a few particular embodiments. The above description, however, is to be considered as illustrative rather than limiting. For example, the physical parameter of the medium to be determined need not be temperature but can be any physical variable which affects the velocity of ultrasound in a known manner. Sound waves of lower frequencies may be substituted for ultrasound depending on the medium and other circumstances. In fact, ultrasound is a wave phenomenon of the same physical nature as sound but with frequencies above the range of human hearing. Where the expression "sound" is used herein, it is to be understood that ultrasound is also included. There are no particular structural requirements on transmitter and receiver transducers. Measurements of time differences such as $t_{TF} - t_{TF}$ may be made by any method inclusive of those by the phase matching techniques known in the optical as well as acoustical arts. In FIGS. 2 and 3, the two transmitter positions T and T' may be collapsed to a single source. The scope of the invention is limited only by the following claims.

What is claimed is:

1. A method of determining the velocity of sound between two field positions F and F' inside a medium which occupies a region including the space between said field positions, said method comprising the steps of
    transmitting a first incident sound beam and a second incident sound beam directed respectively towards said two field positions,
    preselecting two receiver positions R and R' on opposite sides with respect to both said incident beams, and
    detecting for each of said instant beams two scattered sound beams traveling respectively along lines FR and F'R'.

2. The method of claim 1 further comprising the step of comparing for each of said incident beams the transit times of sound between the time of transmission and the times at which said scattered beams are detected at said positions R and R', respectively.

3. The method of claim 1 wherein said first and second incident beams are transmitted respectively from positions T and T', lines TF and T'F' being substantially parallel to each other, TFR and T'F'R' are equal to a predetermined angle.

4. The method of claim 3 wherein said two positions R and R' lie on the plane defined by said positions T, T', F and F'.

5. The method of claim 3 wherein said predetermined angle is between 60 degrees and 120 degrees.

6. The method of claim 3 wherein said predetermined angle is 90 degrees.

7. The method of claim 2 wherein said comparing step involves use of phase matching techniques.

8. The method of claim 1 wherein said medium is a tissue structure.

9. The method of claim 1 wherein said detecting step involves use of transducers.

10. The method of claim 3 or 4 further comprising the step of evaluating the time interval $(t_{TR} + t_{TR'} - t_{TR} - t_{TR'})$ where symbol $t_{AB}$, A and B being dummy indices, denotes the time which it takes for sound to travel from point A to point B.

11. The method of claim 1 wherein said first and second beams are transmitted successively.

* * * * *